United States Patent
Mitchell et al.

(10) Patent No.: US 6,187,318 B1
(45) Date of Patent: Feb. 13, 2001

(54) ANTI-SNORING COMPOSITION

(75) Inventors: Paul S. Mitchell, Boca Raton, FL (US); Gary Robinson, Amherst, NY (US); Paul B. Kravitz, Coral Springs, FL (US)

(73) Assignees: Innovative Chemical Corporation, Amherst, NY (US); MedGen Inc., Davie, FL (US)

( * ) Notice: Under 35 U.S.C. 154(b), the term of this patent shall be extended for 0 days.

(21) Appl. No.: 09/428,876

(22) Filed: Oct. 28, 1999

Related U.S. Application Data

(60) Provisional application No. 60/106,120, filed on Oct. 29, 1998.

(51) Int. Cl.[7] .................................................. A01N 65/00
(52) U.S. Cl. ............................................................ 424/195.1
(58) Field of Search ........................................... 424/195.1

(56) References Cited

U.S. PATENT DOCUMENTS

| | | | |
|---|---|---|---|
| 4,668,513 | * | 5/1987 | Reichert .................................. 424/94 |
| 4,831,057 | * | 5/1989 | Reichert .................................. 514/647 |
| 4,876,283 | * | 10/1989 | Reichert .................................. 514/562 |
| 5,082,665 | * | 1/1992 | Verny ...................................... 424/464 |
| 5,384,118 | * | 1/1995 | Lavalle ................................. 424/70.13 |
| 5,569,679 | * | 10/1996 | Jacob ....................................... 514/711 |
| 5,603,935 | * | 2/1997 | Jian et al. ............................ 424/195.1 |

* cited by examiner

Primary Examiner—Herbert J. Lilling
(74) Attorney, Agent, or Firm—Hodgson Russ Andrews Woods & Goodyear LLP

(57) ABSTRACT

The present invention is directed to a compound for preventing snoring. Essentially, the compound includes various natural oils such as almond oil, olive oil, sunflower oil, and peppermint oil, which serve to lubricate the soft tissue including the uvula and soft palette during sleep. In that manner, the oils dampen the friction of the soft tissue and diminish the noise associated with snoring. The present anti-snoring compound also includes a magnesium-based compound, which helps the oils cling to the soft tissue. If desired, vitamins $B_6$, C and E are also included in the formulation of the present anti-snoring composition, primarily for the health benefit derived from them.

11 Claims, No Drawings

ANTI-SNORING COMPOSITION

CROSS-REFERENCE TO RELATED APPLICATION

The present application claims priority based on provisional application Serial No. 60/106,120, filed Oct. 29, 1998.

BACKGROUND OF THE INVENTION

1. Field of the Invention

The present invention relates to an anti-snoring composition.

2. Prior Art

A National Family Opinion poll conducted in July, 1994 revealed that 90 million Americans over the age of 18 snore and 37 million of those are considered habitual snorers. Interestingly, it was found that snoring is almost twice as common in men as in women. The likelihood of developing a snoring condition also increases with age. Approximately 30% of American males snore at age 30, and about 40% of all Americans snore by the age of 50. Being that there are approximately 290 million Americans, and about 50% are over 50, there are more than 58 million suffering snoring Americans over 50 years of age. Although the problem is common and often not fatal, it is, nonetheless, a medical condition that should be attended to.

SUMMARY OF THE INVENTION

The present invention is directed to a compound for preventing snoring. Essentially, the compound includes various natural oils such as almond oil, olive oil, sunflower oil, and peppermint oil, which serve to lubricate the soft tissue including the uvula and soft palette during sleep. In that manner, the oils damper the friction of the soft tissue and diminish the noise associated with snoring. The present anti-snoring compound also includes magnesium which helps the oils cling to the soft tissue. If desired, vitamins $B_6$, C and E are also included in the formulation of the present anti-snoring composition, primarily for the health benefit derived from them.

DETAILED DESCRIPTION OF THE INVENTION

During sleep, people also breath through their mouth, either in conjunction with breathing through the nose or alternating one to the other. Most people have sufficient space in their throat to allow air to flow easily without producing noise. When this space is reduced, the tissues of the throat, which are soft and collapsible, may come into contact with each other and vibrate as air is drawn between them. When the mouth is opened, which might occur when sleeping on the back, the base of the tongue is positioned further back in the throat, pressing the uvula against the back of the throat. As air passes between these tissues, a vibration is caused between the uvula and the soft palate and snoring occurs. The potential for the narrowing of the airway and the subsequent snoring is greatest during sleep because the throat muscles, tissues and tongue are relaxed, causing the air passageway to narrow.

Sleeping on the back also can cause snoring in that it deprives a person of the normal sleep reflex. Sleeping on the side causes a natural reflex which acts to decongest the nostril on the opposite side, allowing easier breathing through the nasal passage. Sleeping on the back disturbs this normal reflex.

There are some people who during sleep suffer from a complete collapse of the airway leading to the lungs and, consequently, the supply of the air to the lungs is totally blocked off. When this occurs it is called sleep apnea. An apnea is defined as an absence of air flow for about 10 seconds or more. A person with a typical case of sleep apnea has a blockage of breathing of about 10 to 60 seconds at a frequency of five times per hour. Despite the lack of oxygen, the sleeping person is constantly trying to bring air into the lungs, forcing a complete collapse of the tissues of the throat and causing a gasping or snoring-type noise. During this process, the person will have a dangerous drop in blood pressure. This situation can become potentially dangerous.

Under normal circumstances, the apnea is terminated by an arousal, and for the most part is so brief it is hardly remembered. The arousal increases the tone of the muscles in the throat and tongue, thereby releasing the airway blockage and creating a loud grunt or snore. This is usually followed by a period of rapid breathing and again a new apnea occurs.

Obesity is another condition which can cause snoring. Obesity is occasioned by fatty deposits in the throat and a narrowing of the air passage. As the tongue and uvula become enlarged with weight gain, the airway in the throat is reduced, which can exacerbate snoring.

A receding chin, due to a poorly positioned jaw, can also cause a reduction in airway size. Enlarged tonsils or adenoids in children can have the same reducing effect as they do in adults and thus cause snoring in children.

Some drugs can increase snoring by increasing the muscular relaxation in the throat. This is particularly the case with alcohol, tranquilizers, and antihistamines. Many other drugs can cause nasal congestion including certain medications used to treat high blood pressure and prostate disease, as well as the chronic use of some nasal sprays and a variety of irritants, including cigarette smoke.

Whatever the condition causing a person to snore, numerous solutions have been suggested and attempted. The problem is that few solutions work for a period of time sufficient to provide a person with a good and restful night's sleep. It should be stressed that it is important to first diagnose the cause or the underlying reason for snoring. The snoring could simply be caused by a nasal blockage due to a cold, and in that case a nasal spray would be a simple cure. For other causes such as the previously described obesity, receding chin, poorly positioned jaw, enlarged tonsils or adenoids, drugs, alcohol, irritants, sleeping on the back and sleep apnea an anti-snoring composition according to the present invention is extremely beneficial for preventing snoring and providing the person with a relaxed and prolonged nights sleep.

The present anti-snoring composition is typically in the form of an aerosol mist that is sprayed on the back of the throat, tongue and uvula to coat these soft tissues with a lubricating composition which allows for up to ten hours of restful silent sleep.

The ingredients of the present anti-snoring composition are listed in Table 1 below. The composition is comprised of at least one of the group of almond oil, olive oil, peppermint oil, sesame oil and sunflower oil. Other oils useful with the present invention include grape oil, thyme oil, anisi oil, eucalypti oil, camomile oil, menthae oil and terebininiae oil. These oils serve to lubricate the soft tissues in the mouth and throat including the uvula and the soft palate during sleep. Magnesium is important to help retain the various oils on the soft tissue for up to ten hours. In the present invention magnesium is preferably provided in the form of carrageenan (chondrus crispus). This compound is a plant material obtained from various members of the Gigarthineae of Solieriaceae families of red seaweed, Rodophyceae. It is marketed under various brand names of Aquaron, Gencarin, Seaspen and Viscarin. Another preferred compound is magnesium aluminum silicate, which is a complex silicate refined from naturally occuring minerals. It is marketed under various brand names including Gel White, Magnabrite and Veegum. The magnesium compounds have an encapsulating effect that help retain the oils on the soft tissues in the throat throughout the sleep period to continuously prevent the noise associated with snoring. It should be pointed out that while all of the listed oils are preferred for the present composition, they are not all required. What is needed is at least one of the listed oils and a magnesium-based compound to retain the oil in place on the soft tissues of the mouth and throat.

TABLE 1

| INGREDIENTS | BY WEIGHT |
| --- | --- |
| Purified Water | 89.27–57.40 |
| Olive Oil | 3.00–11.00 |
| Ascorbic Acid | .08–.40 |
| Glycerine | 5.00–15.00 |
| Potassium Sorbate | .08–.40 |
| Almond Oil | .40–2.00 |
| Peppermint Oil | .50–2.00 |
| Sesame Oil | 1.00–5.00 |
| Tocopheral Acetate | .05–.30 |
| Pyridoxine HCL | .05–.40 |
| Carrageenan | .10–1.00 |
| Sunflower oil | .50–3.00 |

To this oil-based system is added vitamins $B_6$, C and E. Vitamin $B_6$, also called pyridoxin, is beneficial for the prevention of water retention, and is necessary for the production of hydrochloric acid and the absorption of fats and protein. Also important is the rate that the vitamin plays in cancer immunity. It is an inhibitor of a toxic chemical called homocysteine, which attacks the heart muscle and allows the deposition of cholesterol around the heart.

Vitamin C is an antioxidant that is required for good tissue growth, healthy gums, and adrenal gland function. Commonly known as ascorbic acid, it has been widely praised for its production of anti-stress hormones. Vitamin C also helps to prevent cancer and infection and enhances immunity.

Vitamin E is an antioxidant which is important in preventing cancer and cardiovascular disease. It is widely used to promote blood clotting and healing, and to reduce blood pressure.

The following example describes the manner and process of an anti-snoring composition according to the present invention, and its sets forth the best mode contemplated by the inventors for carrying out the invention, but it is not to be construed as limiting.

EXAMPLE

A double blind study was conducted under medical and clinical criteria and guidelines for such tests. The study had a total of fifty participants. All subjects were in good health except that they experience snoring problems. None of the test subjects was currently taking medication or had a surgical condition which would interfere with the integrity of the study. None of the test subjects had a history of neurological disorders, cardiac, pulmonary, gastrointestinal, liver or kidney disease, or other clinically important diseases.

None of the subjects or the physician administering the study was aware of when and to whom the anti-snoring composition or placebo was being dispensed. The anti-snoring composition was dispensed along with instructions for use, and an evaluation sheet.

The present anti-snoring composition was used over a one week period. Most participants had not used any other anti-snoring product, and none of the participants had seen a physician for the use of an anti-snoring composition. Participants in both the placebo and the anti-snoring composition group were known to have a snoring problem lasting anywhere from two years to 40 years.

The results of participants given the present anti-snoring composition are as follows:

1. Q: How long have you been using the present anti-snoring composition?

| A: 1 night | 2 nights | 3 nights | 4 nights | 5 nights | 6 nights |
| --- | --- | --- | --- | --- | --- |
| 1 | 3 | 15 | 8 | 11 | 1 |

2. Q: Have you used any other products for snoring?
A: No

3. Q: Have you seen a physician for an anti-snoring composition?
A: No

4. Q: How many years have you had a snoring problem?

| A: | Years | Participants | Percentage |
| --- | --- | --- | --- |
| | 1–10yrs. | 11 | 28% |
| | 11–20 yrs. | 16 | 41% |
| | Over 20 yrs. | 10 | 26% |
| | Unknown | 2 | 5% |

5. Q: Has anyone complained about your snoring?

| A: | Participants | Percentage |
| --- | --- | --- |
| Yes | 36 | 92% |
| No | 3 | 8% |

6. Q: Describe your snoring prior to any treatment.

| | Participants | Percentage |
| --- | --- | --- |
| A: a) Loudness (scale from 0 = none, 1 = minimal to 5 loudest) | | |
| 0 | 0 | 0% |
| 1 | 5 | 13% |
| 2 | 3 | 8% |
| 3 | 9 | 23% |
| 4 | 9 | 23% = 79%-loudness complaints |
| 5 | 13 | 33% |
| b) Disruptive (scale from 0 = none, 1 = minimal to 5 loudest) | | |
| 0 | 0 | 0% |
| 1 | 6 | 15% |
| 2 | 5 | 13% |
| 3 | 6 | 15% |
| 4 | 10 | 26% = 72%-disruptive complaints |
| 5 | 12 | 31% |

7. Q: Describe your snoring when using the present anti-snoring composition.

|   | Participants | Percentage |
|---|---|---|
| A: a) Loudness (scale from 0 = none, 1–minimal to 5 loudest) | | |
| 0 | 6 | 15% |
| 1 | 14 | 36% |
| 2 | 12 | 31% = 97% improvement w/present composition |
| 3 | 6 | 15% |
| 4 | 1 | 3% |
| 0 | 0 | 0% |
| b) Disruptive (scale from) = none, 1 = minimal to 5 = loudest) | | |
| 0 | 14 | 35% |
| 1 | 13 | 33% |
| 2 | 5 | 13% = 99% improvement w/present composition |
| 3 | 7 | 18% |
| 4 | 0 | 0% |
| 5 | 0 | 0% |

8. Q: Describe your snoring with other therapies.

A: No other therapies were used.

9. Q: How many times a night does your bed partner's snoring awaken you?

|   | 0 | 1–2 | 3–4 | 5 |
|---|---|---|---|---|
| A: a) with no treatment | 10 | 14 | 13 | 4 |
| b) with present anti-snoring composition | 23 | 10 | 2 | 1 > 92% improvement in sleeping w/present composition |

10. Q: Please evaluate you partner when using the present anti-snoring composition (Table 2) and without (Table 3).

TABLE 2

| | Best to Worst | | | | |
|---|---|---|---|---|---|
| With Present Composition | 1 | 2 | 3 | 4 | 5 |
| 1.Mouth Dryness | 11 | 14 | 5 | 0 | 0 |
| 2.Sleep Quality | 11 | 9 | 7 | 5 | 0 |
| 3.#of Hrs slept | | | 5–9 HRS. | | |
| 4.#of Times Awaken | 11 | 9 | 4 | 0 | 0 |
| 5.Side Effects | | | No Side Effect | | |

TABLE 3

| | Best to Worst | | | | |
|---|---|---|---|---|---|
| WITHOUT | 1 | 2 | 3 | 4 | 5 |
| 1.Mouth Dryness | 1 | 3 | 5 | 4 | 3 |
| 2.Sleep Quality | 2 | 5 | 5 | 5 | 0 |
| 3.#of Hrs slept | | | 3–6 HRS. | | |
| 4.#of Times Awaken | 3 | 3 | 1 | 2 | 0 |
| 5.Side Effects | | | No Side Effect | | |

11. Q: List side effects.

A: No side effect detected.

Results of Participants Given a Placebo are as Follows:

1. Q: How long have you been using?

| A: 1 night | 2 nights | 3 nights | 4 nights | 5 nights | 6 nights |
|---|---|---|---|---|---|
| 1 | 2 | 1 | 4 | 3 | 0 |

2. Q: Have you used any other products for snoring?

A: No

3. Q: Have you asked a physician to prescribe the present anti-snoring composition?

A: No

4. Q: How many years have you had a snoring problem?

| A: | Participants | Percentage |
|---|---|---|
| 1–10 yrs. | 4 | 36% |
| 11–20 yrs. | 5 | 46% |
| Over 20 yrs. | 2 | 18% |

5. Q: Has anyone complained about your snoring?

| A: | Participants | Percentage |
|---|---|---|
| Yes | 9 | 82% |
| No | 2 | 18% |

6. Q: Describe your snoring prior to any treatment.

|   | Participants | Percentage |
|---|---|---|
| A: a) Loudness (scale from 0 = none, 1 = minimal to 5 loudest) | | |
| 0 | 0 | 0% |
| 1 | 4 | 36% |
| 2 | 1 | 10% |
| 3 | 2 | 18% |
| 4 | 0 | 0% = 54%-loudness complaints |
| 5 | 4 | 36% |
| b) Disruptive (scale from 0 = none, 1 = minimal to 5 = loudest) | | |
| 0 | 1 | 10% |
| 1 | 4 | 36% |
| 2 | 2 | 18% |
| 3 | 0 | 0% |
| 4 | 2 | 18% 36%-disruptive complaints |
| 5 | 2 | 18% |

7. Q: Describe your snoring when using the present anti-snoring composition?

|   | Participants | Percentage |
|---|---|---|
| A: a) Loudness (scale from 0 = none, 1 = minimal to 5 loudest) | | |
| 0 | 3 | 27% |
| 1 | 1 | 10% = 68% improvement |
| 2 | 4 | 31% |
| 3 | 2 | 18% |

-continued

| Participants | Percentage |
|---|---|
| 4 | 0 | 0% |
| 5 | 1 | 10% |
| b) Disruptive (scale from 0 = none, 1 = minimal to 5 = loudest) | | |
| 0 | 6 | 54% |
| 1 | 2 | 18% |
| 2 | 2 | 18% |
| 3 | 0 | 0% |
| 4 | 0 | 0% |
| 5 | 1 | 10% |

8. Q: Describe your snoring with other therapies.
A: No other therapies were used.
9. Q: How many times a night does your bed partner's snoring awaken you?

| A: | 0 | 1–2 | 3–4 | 5 |
|---|---|---|---|---|
| a) with no treatment | — | 3 | — | — |
| b) with present anti-snoring composition | — | 1 | — | —> 18% improvement in sleeping w/ placebo |

10. Q: Please evaluate your partner when using the present composition (Table 4) and without (Table 5).

TABLE 4

| With SNORENZ ™ | Best to Worst | | | | |
|---|---|---|---|---|---|
| | 1 | 2 | 3 | 4 | 5 |
| 1.Mouth Dryness | 2 | 3 | 1 | 1 | 2 |
| 2.Sleep Quality | 5 | 1 | 2 | 0 | 1 |
| 3.#of Hrs slept | | | 4–8 HRS. | | |
| 4.#of Times Awaken | 2 | 1 | 1 | 1 | 1 |
| 5.Side Effects | | | No Side Effect | | |

TABLE 5

| WITHOUT SPRAY | Best to Worst | | | | |
|---|---|---|---|---|---|
| | 1 | 2 | 3 | 4 | 5 |
| 1.Mouth Dryness | 1 | 2 | 1 | 0 | 2 |
| 2.Sleep Quality | 3 | 2 | 1 | 0 | 0 |
| 3.#of Hrs slept | | | 6–8 HRS. | | |
| 4.#of Times Awaken | 2 | 1 | 0 | 0 | 0 |
| 5.Side Effects | | | No Side Effects | | |

11. Q: List side effects:
A: No side effects detected.

It should be pointed out that the group administered the placebo experienced some degree of improvement in the sleeping test, however, not to the extent realized by the group administered the present anti-snoring composition. Also, in the Example under the section setting forth the results of the participants given a placebo, there are references to use of the present anti-snoring composition. In fact, these participants did not receive the present composition because they were the placebo group. Nonetheless, they believed they were being treated with the present composition, thus the somewhat improved results.

It is appreciated that various modifications to the present inventive concepts described herein may be apparent to those of ordinary skill in the art without departing from the spirit and scope of the present invention as defined by the herein appended claims.

What is claimed is:

1. A composition for the prevention of snoring, the composition having active ingredients which consist of:
    a) a natural oil selected from the group consisting of olive oil, almond oil, peppermint oil, sesame oil, sunflower oil, grape oil, thyme oil, anisi oil, eucalypti oil, camomile oil, menthae oil, terebinthiniae oil, and mixture thereof;
    b) a vitamin selected from the group consisting of $B_6$, C and E; and
    c) a magnesium-based compound selected from carrageenan and magnesium aluminun silicate, wherein the magnesium-based compound is effective to maintain the composition on the throat to prevent snoring.

2. The composition of claim 1 wherein the olive oil is present, by volume, in a range of about 3.0% to about 11.0%.

3. The composition of claim 1 wherein the almond oil is present, by volume, in a range of about 0.4% to about 2.0%.

4. The composition of claim 1 wherein the peppermint oil is present, by volume, in a range of about 0.5% to about 2.0%.

5. The composition of claim 1 wherein the sesame oil is present, by volume, in a range of about 1.0% to about 5.0%.

6. The composition of claim 1 wherein the sunflower oil is present, by volume, in a range of about 0.5% to about 3.0%.

7. A composition for the prevention of snoring, which consists of:
    a) olive oil present, by volume, in a range of about 3.0% to about 11.0%;
    b) a vitamin selected from the group consisting of $B_6$, C and E; and
    c) a magnesium-based compound selected from carrageenan and magnesium aluminum silicate, wherein the magnesium-based compound is effective to maintain the composition on the throat to prevent snoring.

8. A composition for the prevention of snoring, which comprises:
    a) almond oil present, by volume, in a range of about 0.4% to about 2.0%;
    b) a vitamin selected from the group consisting of $B_6$, C and E; and
    c) a magnesium-based compound selected from carrageenan and magnesium aluminum silicate, wherein the magnesium-based compound is effective to maintain the composition on the throat to prevent snoring.

9. A composition for the prevention of snoring, which comprises:
    a) peppermint oil present, by volume, in a range of about 0.5% to about 2.0%;
    b) a vitamin selected from the group consisting of $B_6$, C and E; and
    c) a magnesium-based compound selected from carrageenan and magnesium aluminum silicate, wherein the magnesium-based compound is effective to maintain the composition on the throat to prevent snoring.

10. A composition for the prevention of snoring, which comprises:
    a) sesame oil present, by volume, in a range of about 1.0% to about 5.0%;
    b) a vitamin selected from the group consisting of $B_6$, C and E; and c) a magnesium-based compound selected from carrageenan and magnesium aluminum silicate, wherein the magnesium-based compound is effective to maintain the composition on the throat to prevent snoring.

11. A composition for the prevention of snoring, which comprises:

a) sunflower oil present, by volume, in a range of about 0.5% to about 3.0%;

b) a vitamin selected from the group consisting of $B_6$, C and E; and c) a magnesium-based compound selected from carrageenan and magnesium aluminum silicate, wherein the magnesium-based compound is effective to maintain the composition on the throat to prevent snoring.

\* \* \* \* \*